US009917898B2

(12) United States Patent
Keating et al.

(10) Patent No.: US 9,917,898 B2
(45) Date of Patent: Mar. 13, 2018

(54) HYBRID DENTAL IMAGING SYSTEM WITH LOCAL AREA NETWORK AND CLOUD

(71) Applicant: Dental Imaging Technologies Corporation, Hatfield, PA (US)

(72) Inventors: Robert E. Keating, Chalfont, PA (US); Bradley S. Carlson, Doylestown, PA (US); Darryl Day Spencer, Furlong, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 289 days.

(21) Appl. No.: 14/697,006

(22) Filed: Apr. 27, 2015

(65) Prior Publication Data

US 2016/0316015 A1 Oct. 27, 2016

(51) Int. Cl.
*G06T 9/00* (2006.01)
*H04L 29/08* (2006.01)
(Continued)

(52) U.S. Cl.
CPC ........... *H04L 67/1097* (2013.01); *A61B 6/14* (2013.01); *A61B 6/5205* (2013.01);
(Continued)

(58) Field of Classification Search
CPC combination set(s) only.
See application file for complete search history.

(56) References Cited

U.S. PATENT DOCUMENTS

| 4,628,356 A | 12/1986 | Spillman et al. |
| 5,117,445 A * | 5/1992 | Seppi .................... A61B 6/032 |
| | | 378/19 |

(Continued)

FOREIGN PATENT DOCUMENTS

| JP | 2004313561 A | 11/2004 |
| WO | 0161613 A1 | 8/2001 |
| WO | 2013136093 A2 | 9/2013 |

OTHER PUBLICATIONS

Extended European Search Report from the European Patent Office for Application No. 16166731.6 dated Sep. 22, 2016 (8 pages).

(Continued)

*Primary Examiner* — Tsung-Yin Tsai
(74) *Attorney, Agent, or Firm* — Michael Best & Friedrich LLP

(57) ABSTRACT

Methods and systems for storing and accessing dental images. The system includes an imaging system for acquiring x-ray projection frames. The imaging system is connected to a local server through a local area network. A cloud server communicates with devices on the local area. The x-ray projection frames are transmitted from the imaging system to the local server. The local server stores the series of related x-ray projection frames according to a specified policy. In one embodiment, the x-ray projection frames are compressed into a compressed image data set using a modified video compression prediction algorithm customized for x-ray images. The x-ray image data (whether compressed or not) is transmitted to the cloud server for storage. The x-ray image data can be accessed from the cloud server by external devices and by other local area networks.

9 Claims, 6 Drawing Sheets

(51) Int. Cl.
*H04N 19/142* (2014.01)
*H04N 19/172* (2014.01)
*H04N 19/50* (2014.01)
*G06T 11/00* (2006.01)
*A61B 6/14* (2006.01)
*A61B 6/00* (2006.01)

(52) U.S. Cl.
CPC .......... *G06T 11/005* (2013.01); *G06T 11/008* (2013.01); *H04N 19/142* (2014.11); *H04N 19/172* (2014.11); *H04N 19/50* (2014.11)

(56) References Cited

U.S. PATENT DOCUMENTS

| | | | |
|---|---|---|---|
| 5,434,418 A | 7/1995 | Schick | |
| 6,049,584 A | 4/2000 | Pfeiffer | |
| 6,067,075 A | 5/2000 | Pelanek | |
| 6,196,715 B1* | 3/2001 | Nambu | A61B 6/00 378/11 |
| 6,771,822 B1 | 8/2004 | Brackett | |
| 6,850,252 B1* | 2/2005 | Hoffberg | G06K 9/00369 348/E7.061 |
| 6,909,436 B1* | 6/2005 | Pianykh | G06T 11/008 345/581 |
| 6,937,767 B1 | 8/2005 | Burak et al. | |
| 6,983,064 B2 | 1/2006 | Song | |
| 7,327,866 B2 | 2/2008 | Bae et al. | |
| 7,751,871 B2 | 7/2010 | Rubbert | |
| 7,801,382 B2 | 9/2010 | Hernandez et al. | |
| 8,257,653 B2 | 9/2012 | Drucker et al. | |
| 8,300,964 B2 | 10/2012 | Crucs | |
| 8,577,163 B2 | 11/2013 | Natanzon et al. | |
| 9,613,440 B2* | 4/2017 | Claus | G06T 11/006 |
| 9,629,602 B2* | 4/2017 | Do | |
| 2002/0016821 A1 | 2/2002 | Son et al. | |
| 2004/0022447 A1 | 2/2004 | Mukhopadhyay et al. | |
| 2006/0002509 A1* | 1/2006 | Claus | G06T 11/005 378/21 |
| 2007/0003118 A1* | 1/2007 | Wheeler | G06T 7/001 382/128 |
| 2007/0014448 A1* | 1/2007 | Wheeler | G06T 7/0012 382/128 |
| 2007/0036442 A1 | 2/2007 | Stoffer et al. | |
| 2007/0226005 A1 | 9/2007 | Smith et al. | |
| 2008/0004097 A1 | 1/2008 | Maya et al. | |
| 2008/0006282 A1 | 1/2008 | Sukovic et al. | |
| 2008/0097794 A1 | 4/2008 | Arnaud et al. | |
| 2009/0208086 A1 | 8/2009 | Pelc | |
| 2010/0054400 A1* | 3/2010 | Ren | A61B 6/025 378/37 |
| 2010/0246945 A1* | 9/2010 | Inoue | H04N 19/172 382/165 |
| 2011/0029488 A1 | 2/2011 | Fuerst et al. | |
| 2011/0170789 A1 | 7/2011 | Amon et al. | |
| 2012/0015825 A1* | 1/2012 | Zhong | G01N 21/6428 506/6 |
| 2012/0082356 A1* | 4/2012 | Zankowski | G06T 9/00 382/131 |
| 2012/0095923 A1 | 4/2012 | Herlitz | |
| 2012/0237101 A1 | 9/2012 | Kaempfer et al. | |
| 2012/0265050 A1* | 10/2012 | Wang | A61B 5/055 600/411 |
| 2012/0278094 A1 | 11/2012 | Kovacevic et al. | |
| 2013/0208955 A1 | 8/2013 | Zhao et al. | |
| 2013/0208966 A1 | 8/2013 | Zhao et al. | |
| 2013/0266079 A1* | 10/2013 | Huang | H04N 19/00903 375/240.26 |
| 2014/0126800 A1 | 5/2014 | Lang et al. | |
| 2014/0223352 A1* | 8/2014 | Natanzon | G06F 19/321 715/771 |
| 2015/0228092 A1* | 8/2015 | Claus | G06T 11/006 382/131 |
| 2015/0335306 A1* | 11/2015 | Do | A61B 6/032 378/19 |

OTHER PUBLICATIONS

Jones, "Radiology Department Services PACS Project", Portsmouth Hospitals NHS, http://www.solentsupplies.nhs.uk/departments/Wards-and-Departments/radiology—pacs-projects, 2 pages, 2006-2013, Portsmouth Hospitals NHS Trust.
Wegener, "Compressing the Storage Demands for CT Imaging", MDT Medical Design Technology, Sep. 10, 2007, http://www.mdtmag.com/articles/2007/09/compressing-storage-demands-ct-imaging, 5 pages.
"Medical Imaging", Wikipedia, 14 pages, last modified Jun. 24, 2015, https://en.wikipedia.org/wiki/Medical_Imaging.
Strickland, Nicola, "PACS (picture archiving and communication systems): filmless radiology", Archives of Disease in Childhood, Jan. 5, 2000, 7 pages, http://adc.bmj.com/content/83/1/82.full.html.
"Picture archiving and communication system", Wikipedia, 7 pages, last modified Jun. 11, 2015, https://en.wikipedia.org/wiki/Picture_archiving_and_communication_system.

* cited by examiner

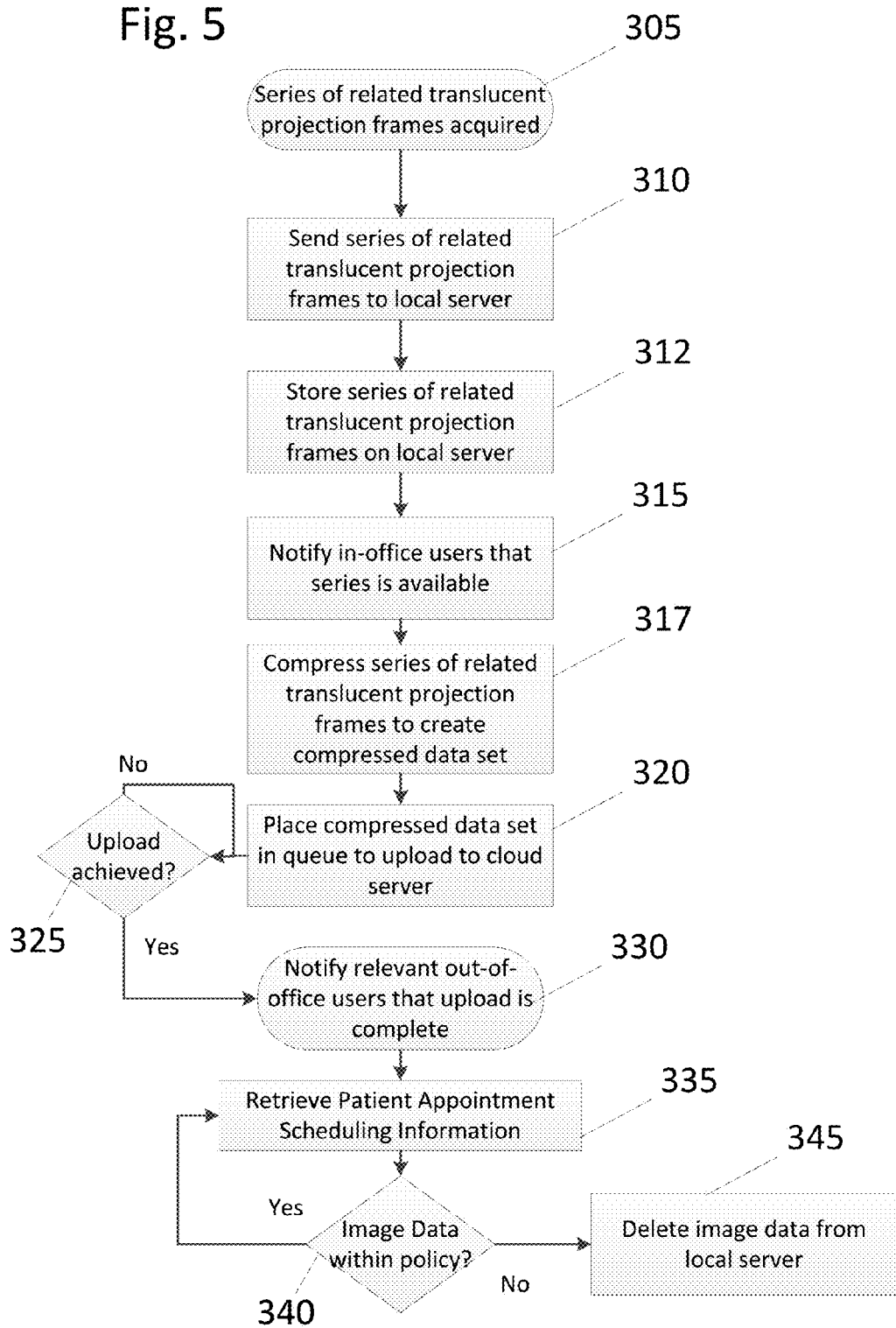

HYBRID DENTAL IMAGING SYSTEM WITH LOCAL AREA NETWORK AND CLOUD

FIELD

Embodiments of the invention relate to acquiring, storing, and accessing dental images.

BACKGROUND

Many images are taken at dental offices on a daily basis. Such images can include two-dimensional x-ray projections that are reconstructed into three-dimensional volumetric images. These three-dimensional images can have a relatively large file size. As a consequence, the files are often difficult to store and access.

SUMMARY

Internet-based cloud storage systems are widely available and offer scalability. As a consequence, data storage of x-ray images on an Internet-based cloud system has been proposed by others. However, current Internet-based cloud data storage systems have numerous deficiencies, especially when application of such systems to a dental office imaging system is considered.

Upload and download times can be problematic because numerous devices may be attempting to upload or download large amounts of data at the same time. Residential and small business Internet connections often have an upload speed that is slower than the download speed. This asymmetric characteristic is problematic because many devices (e.g., x-ray machines) may be attempting to transmit large amounts of data to the cloud system within the same time period. This can create a bottleneck of data to be uploaded. Dentists cannot wait extended periods of time for data to upload before taking additional images.

Additionally, a reliable connection is required at all times in order to maintain an operational dental imaging system because if data is transmitted while the dental office is not connected to the cloud, the data will be lost. Cloud servers may be unavailable if the cloud crashes or if the Internet connection suffers a failure.

Accordingly, in some embodiments, the invention provides systems and methods for storing and accessing dental images in a manner designed to reduce or overcome many of the noted problems. Some embodiments of the invention use a server on a local area network (LAN) in combination with an Internet-based cloud server to minimize upload problems created by large amounts of data, slow upload times, and/or unreliable Internet connectivity. Some embodiments of the invention store specified data on a local server for quick and efficient access in the dental office.

Certain embodiments of the invention increase upload and download speeds by using modified video compression techniques. In some embodiments of the invention, video compression is used on a series of two-dimensional, x-ray dental images. Embodiments of the invention utilize data compression with a modified prediction algorithm customized for x-ray images. As discussed in greater detail below, the term "translucent" is used to describe the images processed in embodiments described herein because the radiation to which the imaged object is exposed passes (at least partially) through the imaged object and the resulting image, for example, when produced on film, has certain translucent properties or characteristics.

Certain embodiments of the invention allow dental images to be accessed from multiple locations both inside and outside a dental office. Embodiments of the invention provide scalability and wide availability of cloud server data storage while also providing improved upload speed.

Certain embodiments of the invention queue data uploads on a server on the LAN until upload to the cloud server is achieved. Thus, dentists do not need to wait for data to upload to the cloud before capturing additional data. Certain embodiments of the invention allow queued images on the LAN server to be uploaded after normal business hours if necessary. Additionally, certain embodiments of the invention allow dentists to continue collecting data (e.g., taking x-rays) when Internet access fails or when a cloud service provider or component crashes or is down, because data to be uploaded can be stored on the local server until the Internet connection or cloud is restored.

Embodiments of the invention cache download requests on the LAN server until they can be fulfilled by the cloud server. Some embodiments of the invention use the same application interface supported by both the LAN and cloud servers so that client software can connect to the LAN server when inside the dental office or to the cloud server when outside the dental office.

In one exemplary embodiment, the invention provides a method of managing x-ray image data. The method includes acquiring the x-ray image data. The x-ray image data is associated with a first patient. The method also includes storing the x-ray image data on an x-ray acquisition computer, transmitting the x-ray image data to a local server from the x-ray acquisition computer, storing the x-ray image data on the local server, transmitting the x-ray image data from the local server to a remote server, and storing the x-ray image data on the remote server. The method also includes retrieving patient appointment scheduling information from an electronic patient scheduling calendar. The patient appointment scheduling information includes at least one of an amount of time elapsed since a most recent visit of the patient and an amount of time until a next expected visit of the patient. The method also includes automatically deleting the x-ray image data from the local server when at least one condition is satisfied. The at least one condition is based on the patient appointment scheduling information.

In another exemplary embodiment, the invention provides a system for storing and accessing medical images. The system includes an imaging system configured to acquire a series of related x-ray frames associated with a patient. A local server is connected to the local area network. The system also includes a local server connected to the imaging system and configured to receive the series of related x-ray frames, store the series of related x-ray frames according to a specified policy, and transmit the series of related x-ray images to a remote server. The specified policy includes deleting the x-ray frames from the local server when at least one condition is satisfied. The at least one condition is based on at least one of an amount of time elapsed since a most recent visit of the patient, an amount of time elapsed since a most recent access of data associated with the patient, an amount of time until a next expected visit of the patient, and an amount of available storage space on the local server.

The system may also include compressing the series of related x-ray frames to create a compressed image data set, and placing the compressed image data set in the upload queue.

The system may also include a cloud server configured to communicate to the local server. The cloud server receives the series of related x-ray frames from the upload queue, and stores the x-ray frames. The x-ray frames may be compressed prior to transmission and storage. Thus, the cloud server may be configured to receive compressed data sets and store the compressed data sets.

In another embodiment, the invention provides a method of storing and accessing medical images. The method includes creating a series of related x-ray image data using an imaging system. The imaging system is connected to a local area network and the x-ray image data is associated with a patient. The method also includes sending the series of related x-ray frames from the imaging system to a local server, where the local server is connected to the local area network. The method also includes storing the series of related x-ray frames on the local server according to a specified policy; and transmitting the series of related x-ray frames outside the local area network for storage.

The method may also include compressing the series of x-ray related projection frames to create a compressed image data set prior to sending the series of related x-ray projection frames outside the local area network for storage. Alternatively, the series of related x-ray projection frames may be compressed prior to storing the series of related x-ray projection frames on the local server.

In yet another embodiment, the invention provides a system for processing x-ray image data. The system includes an imaging system. The imaging system is configured to acquire x-ray image data. The x-ray image data includes a plurality of x-ray frames, and the plurality of x-ray frames includes first and second frames. The system also includes a codec. The codec is configured to receive the x-ray image data from the imaging system and compress the plurality of x-ray projection frames to generate a compressed data set by performing at least one of computing a difference between the first and second frames, and predicting at least one pixel of the second frame based on at least one pixel of the first frame.

In another embodiment, the invention provides a method of processing x-ray data. The method includes acquiring a plurality of x-ray projection frames of at least one object representing at least a portion of a patient and compressing the plurality of x-ray projection frames to generate a compressed data set. The plurality of x-ray projection frames includes first and second frames. Compressing the plurality of x-ray projection frames includes at least one of computing a difference between the first and second frames, and predicting at least one pixel of the second frame based on at least one pixel of the first frame.

Other aspects of the invention will become apparent by consideration of the detailed description and accompanying drawings.

BRIEF DESCRIPTION OF THE DRAWINGS

FIG. 5 is a schematic diagram of a method of uploading an image to a cloud server implemented by the hybrid system of FIG. 1.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
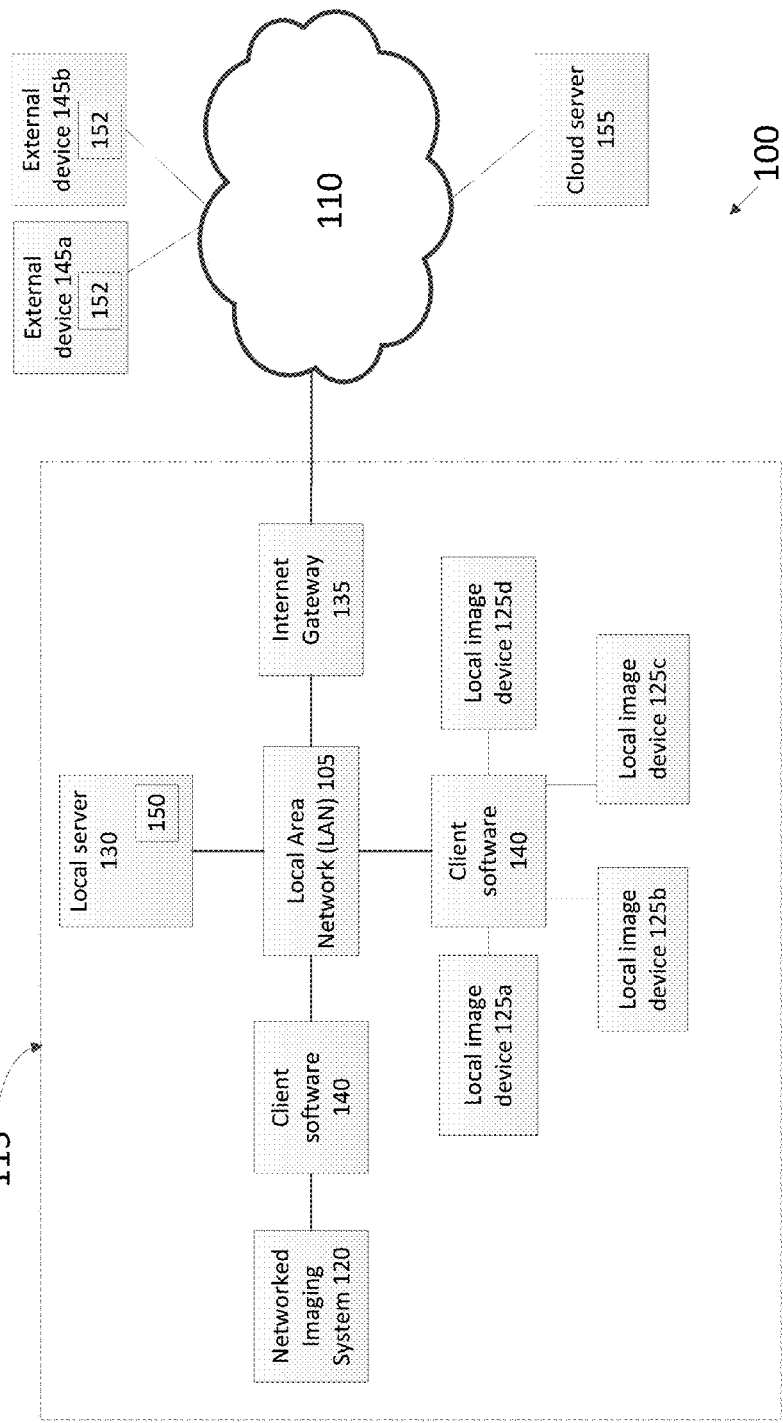
FIG. 1 illustrates a block diagram of a hybrid system for storing and accessing dental images from within a dental office or outside the dental office.

FIG. 1 illustrates a hybrid system 100 for acquiring, storing and accessing data associated with dental images using a local area network (LAN) 105 in combination with components connected to the LAN 105 via a network 110, for example, the Internet. Since dental offices often acquire several dental images associated with patients of the dental office, the hybrid system 100 may be implemented in a dental office to facilitate the storage and management of dental images associated with a plurality of patients. The hybrid system 100 allows a user to store a large number of dental images associated with a patient by using unique compression techniques. The hybrid system 100 also allows a user to access the stored dental images inside and outside a specific dental office. This may allow, for example, a patient to access his/her dental images even when he/she is not in the dental office using, for example, a mobile application that connects the patient to the hybrid system 100.

The hybrid system 100 includes a dental office 115 having at least one networked imaging system 120, at least one local image device 125, and a local server 130. The dental office 115 also includes the LAN 105 that connects to the networked imaging system 120, the local image device 125, and the local server 130. The local image device 125 may be, for example, a computer running client software 140. In the illustrated embodiment, the hybrid system 100 includes a plurality of local image devices 125a-d. In other embodiments, the hybrid system 100 only includes a single local image device 125a-d. The networked imaging system 120 and local image devices 125a-d connect to the LAN 105 via client software 140. Client software 140 can receive data from the LAN 105. Furthermore, client software 140 can reconstruct a series of related x-ray projection frames into a three-dimensional volumetric image. Client software 140 may also be capable of sending and receiving a series of related x-ray projection frames as well as three-dimensional volumetric images. The local server 130 is also connected to the LAN 105 and stores information, for example, dental images associated with patients of the dental office 115. The local server 130 communicates with the networked imaging system 120 and the local image devices 125a-d through the LAN 105. The hybrid system 100 further includes an Internet gateway 135. The Internet gateway 135 connects the LAN 105 to the network 110, which allows the local server 130, the networked imaging system 120, and the local image devices 125a-d to communicate with the components connected to the network 110. Sometimes the components connected to network 110 alone or together with the network 110 are referred to as a "cloud." The network 110 is connected to at least one cloud server 155 and can be connected to at least one external image device 145 outside the dental office 115. In the illustrated embodiment, the network 110 is connected to a plurality of external image devices 145a-b.

The types of devices and number of devices used in the hybrid system 100 can vary in alternate embodiments. For example, although only one dental imaging machine 200 and only one networked imaging system 120 are pictured in FIG. 1, alternate embodiments of the invention may include multiple dental imaging machines 200 and/or multiple networked imaging systems 120. Furthermore, in some embodiments, the hybrid system 100 can include at least one networked imaging system 120 or at least one local image device 125 but not both.

Figure 2:
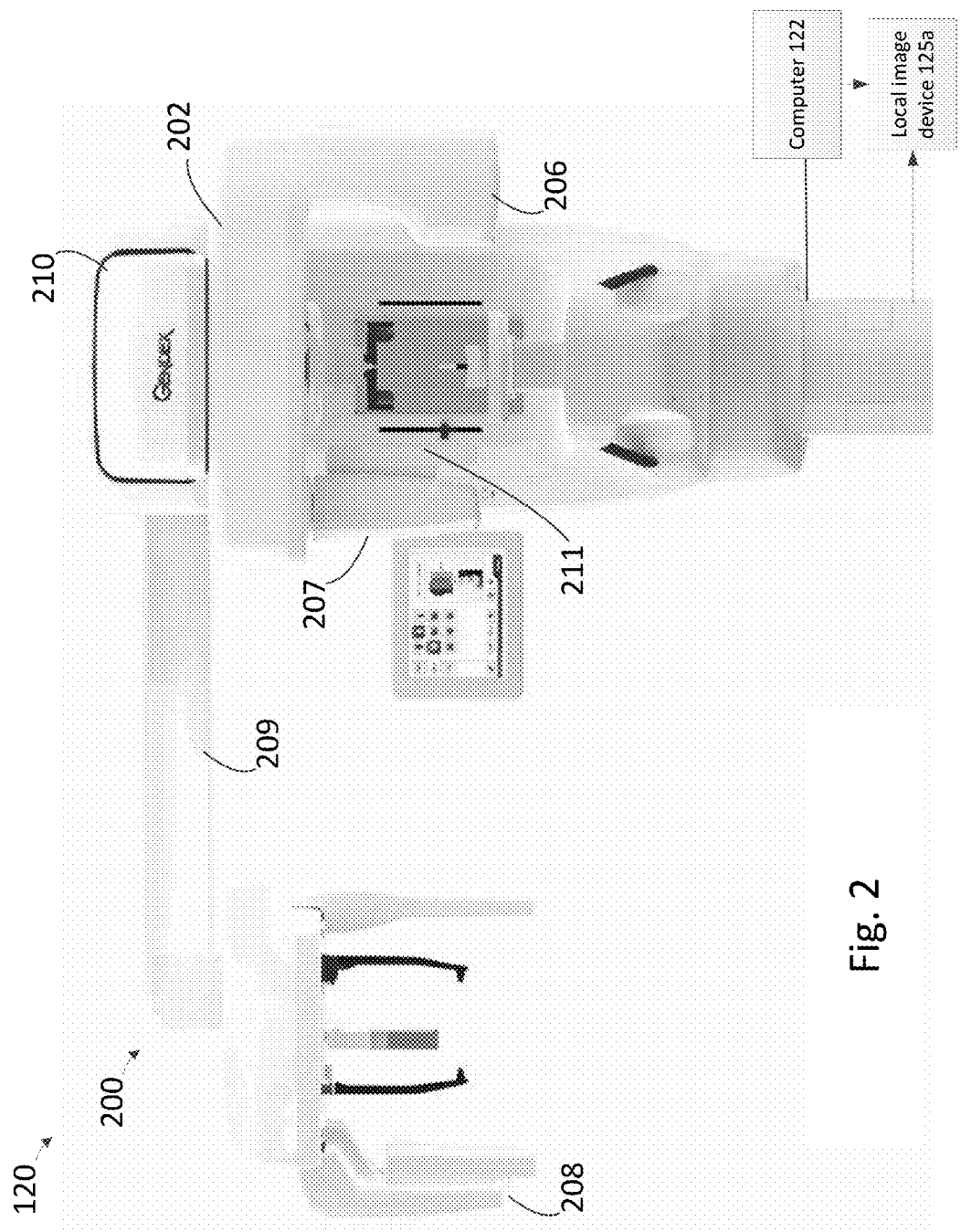
FIG. 2 illustrates a networked imaging system of the hybrid system of FIG. 1.

As shown in FIG. 2, the networked imaging system 120 includes a dental imaging machine 200 (e.g., an x-ray machine capable of capturing images for cone beam computed tomography ("cone beam CT" or "CBCT"), for panoramic imaging, or for cephalometric imaging) and a local image device 125a. The dental imaging machine 200 acquires x-ray image data associated with a patient. The x-ray image data from the imaging machine may be, for example, in the form of a series of related x-ray projection frames. In the illustrated embodiment, the network imaging system 120 also includes a computer 122. The computer 122 controls the dental imaging machine 200 and may run client software 140 to connect the dental imaging machine 200 to the LAN 105. In the case of cone beam CT imaging, the computer 122 processes the x-ray projection frames to produce a three-dimensional, volumetric image of a portion of the patient. In some embodiments, the computer 122 is also referred to as an acquisition computer. In some embodiments the local image device 125a is referred to as a viewing computer. In the illustrated embodiment, the local image device 125a is connected to the computer 122 (e.g., via USB or Firewire) to allow the series of related x-ray projection frames or the three-dimensional volumetric image to be viewed. Although computer 122 is pictured in FIG. 2, in some embodiments, the local image device 125a is connected to the dental imaging machine 200 and runs client software 140 to connect to the LAN 105. In other embodiments, the dental imaging machine 200 runs client software 140 and connects to the LAN 105 without using computer 122 or local image device 125a. In embodiments in which the dental imaging machine 200 includes an internal image-processing computer (not shown) that runs client software 140 and connects to the LAN 105 without the computer 122 or the local image device 125a, the internal image-processing computer within the dental imaging machine 200 can be referred to as an acquisition computer.

In the illustrated embodiment, the dental imaging machine 200 is configured to acquire panoramic, three-dimensional, and cephalometric dental scans. The dental imaging machine 200 includes an x-ray source 206, a first x-ray image detector 207, a second x-ray image detector 208, and a third x-ray detector 211. In the illustrated embodiment, each x-ray image detector 207, 208, 211 captures a different type of x-ray image (e.g., CT image, panaromic image, or cephalometric image). The x-ray source 206 and the first x-ray image detector 207 are mounted on a gantry 202 coupled to a support arm 210 and the first x-ray image detector 207 is positioned directly opposite the x-ray source 206. In some embodiments, a patient is positioned between the x-ray source 206 and the first x-ray image detector 207 so that the dental imaging machine 200 can capture an x-ray image of at least a portion of the patient. The gantry 202 rotates about the patient. As the support arm 210 rotates around the patient, the x-ray source 206 and the x-ray image detector 207 acquire a plurality of x-ray projection frames (commonly referred to as "projection frames") of the patient. For example, the support arm 210 is first placed at a first angle and the x-ray source 206 and the first x-ray image detector 207 acquire a first x-ray projection frame of the patient. The support arm 210 then rotates and is positioned at a second angle different than the first angle. The x-ray source 206 and the first x-ray image detector 207 then acquire a second x-ray projection frame of the patient at the second angle. The x-ray source 206 and the first x-ray image detector 207 can rotate relative to the patient and obtain a plurality of x-ray projection frames. Because of the rotation of the support arm 210 about the patient, the x-ray source 206 and the first x-ray image detector 207 can capture panoramic dental images. The x-ray projection frames captured by the x-ray source 206 and the first x-ray image detector 207 can also be used to construct a three-dimensional model of at least a portion of the patient.

The second x-ray image detector 208 is supported by a beam 209 and positioned opposite the x-ray source 206. The second x-ray image detector 208 of the dental imaging machine 200 can perform cephalometric dental scans. A screen is positioned between the x-ray source 206 and the second x-ray image detector 208. Typically, a patient is positioned between the second x-ray image detector 208 and the screen. The screen is then able to control the amount of x-ray radiation reaching the patient. For example, the screen is movable and can be positioned such that only the area immediate the patient's mouth receives x-ray radiation. Thus, the screen is configured to minimize the patient exposure to x-ray radiation and perform cephalometric dental scans.

The x-ray projection frames obtained through the dental imaging machine 200 represent at least a portion of a patient and/or one object within the patient. In some embodiments, the x-ray projection frames are associated with the same patient and are simply taken at distinct angles relative to the patient. In other embodiments, a first projection frame and a second projection frame may be related in a different manner. For example, the first frame may be taken at a first period of time and the second frame may be taken at a second period of time different from the first period of time. Because the x-ray projection frames obtained for even just one patient often require large amounts of storage space, the hybrid system 100 uses video compression techniques to compress the x-ray image data associated with patients of the dental office 115. Examples of suitable compression algorithms include, but are not limited to, H.264, H.265, CABAC, CAVLC, and Exp-Golomb.

The hybrid system 100 includes a modified video codec 150 to compress the series of related x-ray projection frames according to a modified video compression technique. The modified video codec 150 can include software, hardware, or a combination of software and hardware. The modified video compression technique uses a modified inter-frame prediction algorithm. Compressing the series of related x-ray projection frames using the inter-frame prediction algorithm increases the compression ratio of the image data in comparison to compressing each raw image projection frame individually. In the illustrated embodiment, the codec 150 is located in the local server 130. In other embodiments, the codec 150 is located on other parts of the hybrid system 100 (e.g., within the acquisition computer 122 or the client software 140). In general terms, the networked imaging system 120 includes a processor, memory, and instructions, an ASIC, or other component (generically referred to as a "codec") that implements the logic and functions of the modified video codec 150.

Known digital video compression techniques use prediction algorithms that assume that the image data being compressed is data from a reflective imaging process. For example, known prediction algorithms, assume that a series of images is from a video camera, in which visible light reflects off an object and the light is captured as an image on, for example, an electronic sensor. X-ray images (as compared to video images) are sometimes referred to as "translucent" because radiation in the form of x-ray radiation passes (at least partially) through the imaged object. The resulting image, when produced on film, for example, has certain translucent properties or characteristics. Therefore, x-ray images are not reflective images and the inter-frame prediction algorithm in accordance with the invention has the benefit, for example, of compressing the image data more efficiently than a conventional algorithm.

In addition, certain known digital video compression techniques assume singular (i.e., one-directional) motion about a center axis when numerous images are taken at rotating angles around an object. However, a series of raw x-ray image projection frames introduces two-fold motion about a center axis because x-rays produce translucent images rather than reflective images. For example, unlike imaging techniques in which the object is opaque to and/or reflective of to the incident light, an x-ray image reveals features both in front of and behind the axis of rotation, and the features in the back move in a direction different from that of the features in the front. Thus, the modified inter-frame prediction algorithm that accounts for the translucent nature of the images and this two-fold motion further improves compression ratio by reducing the error of predictions between each raw x-ray image projection frame.

Figure 3:
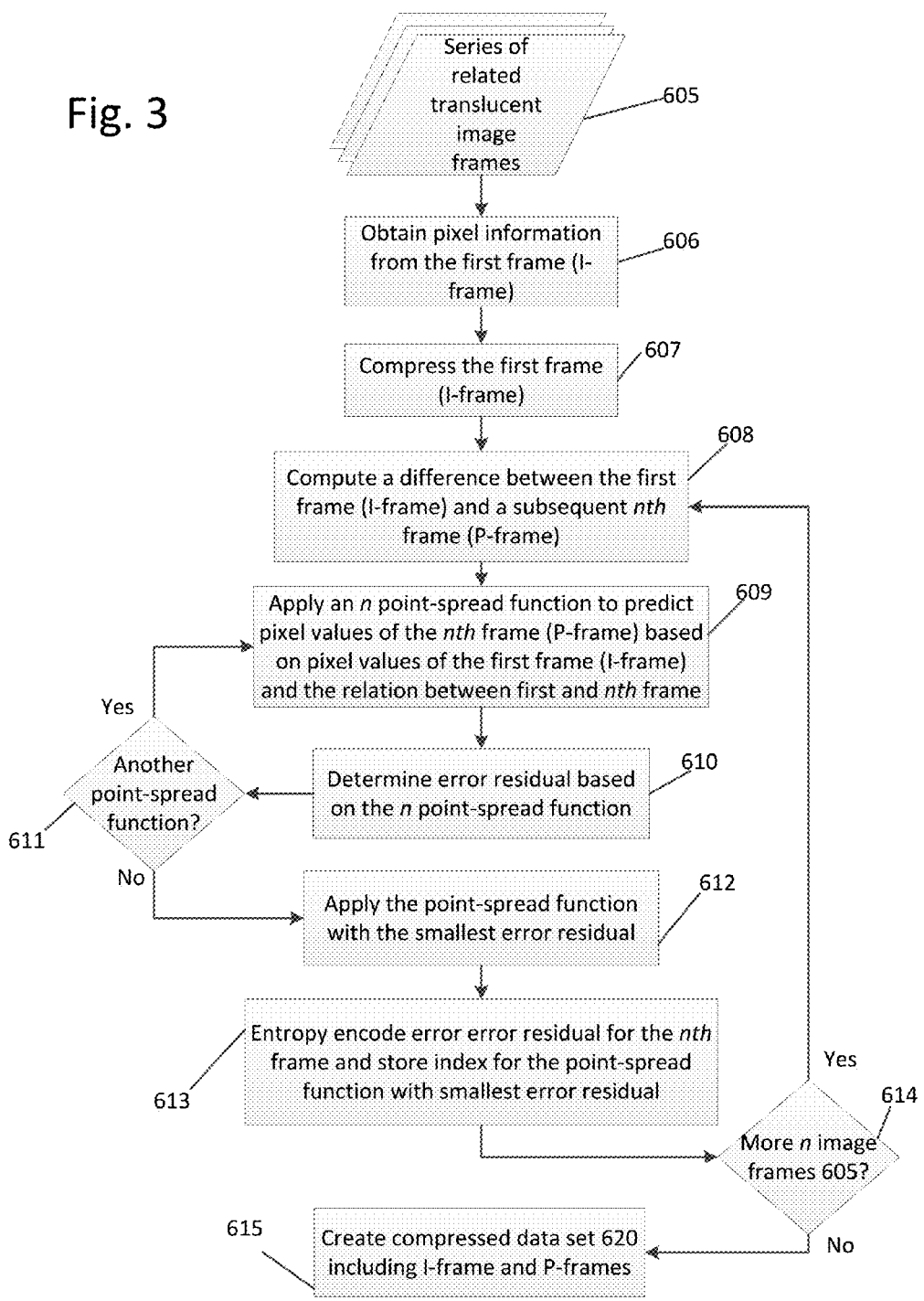
FIG. 3 is a schematic diagram of a compression method implemented by the hybrid system of FIG. 1.

The modified prediction algorithm exploits the relationships between pixel values in sequential x-ray image projection frames. Some projection frames are compressed as intra-coded frames (also referred to as "intra-frames" or "I-frames") and other projection frames are compressed as predictive frames (P-frames). I-frames are expressed independently from any other frames and serve as a basis for P-frames to reference to increase compression ratios of the P-frames. Stated another way, periodic I-frames in the compressed sequence allow for decompressing a subset of P-frames saved between multiple I-frames (i.e., details of P-frames can be determined from related I-frames). The first compressed projection frame of FIG. 3 is considered an I-frame, and subsequent n projection frames can be either I-frames or P-frames. Unlike existing video compression techniques (e.g., MPEG, H.265, etc.), P-frames of the present invention include point-spread function indexes, which will be described in greater detail below.

More specifically, a pixel value from a particular projection frame (e.g., an I-frame) in the series of related x-ray projection frames represents the cumulative x-ray density of the material along the ray from the x-ray source 206 to the corresponding location on a detector panel. This pixel value tends to be distributed according to a transfer function (sometimes also referred to as a "point-spread function" in image processing) among neighboring pixels in subsequent projection frames due to the rotation of the x-ray source 206 and detector apparatus 207 about the object. In some embodiments, the improved, modified prediction algorithm uses a library of point-spread functions to predict pixel values in successive image projection frames, providing a more accurate estimate than the prediction algorithms implemented in current video compression standards designed for reflective imaging modalities. Transfer functions suitable for a particular image type can be generated, for example, by a Monte Carlo simulation. In other embodiments, only one point-spread function is used to compress the successive image projection frames. The x-ray source 206 and the x-ray image detector 207 acquire a first x-ray projection frame at a first angle and a second x-ray projection frame at a second angle. At least one pixel in the second x-ray projection frame is predicted based on the first and the second angles and the first x-ray projection frame. The point-spread function with the smallest error residual is used, and its index within the library is stored in the compressed image data set 620, followed by an entropy-encoded error residual for the image. The more accurate, modified prediction algorithm results in smaller error residual, which allows for higher compression in the entropy-encoding stage of the compression algorithm.

FIG. 3 illustrates the modified video compression technique using the modified prediction algorithm where a series of related x-ray projection frames is compressed. First, the dental imaging machine 200 acquires a series of related n x-ray projection frames 605 (i.e., each image projection frame taken at a particular angle around a patient's jaw). At step 606, pixel information from a first x-ray projection frame is obtained. The first x-ray projection frame is an I-frame, since it is not expressed based on any other frames. Optionally, at step 607, the first projection frame, which can for example be an I-frame, of the series of related x-ray projection frames 605 is compressed using an image-compression algorithm. The image-compression algorithm can, for example, be a JPEG-based or other conventional image-compression algorithm. Subsequent image projection frames, also referred to as P-frames, are then compressed using the modified prediction algorithm that relates pixels in the image projection frame to be compressed with pixels in previous image projection frames (steps 610-615). Optionally, before the prediction algorithm is applied, each projection frame can be individually compressed in the same manner as was done with the first projection frame. Thus, the set of projection frames can optionally be compressed in two ways, namely separately as individual images and together as a sequence of related images. In any case, at step 608, a difference between the first projection frame and a subsequent n projection frame is computed. Particularly, the relation between the first projection frame and the subsequent n projection frame is determined. For example, the angle difference between the first frame and the subsequent n projection frame is calculated. At step 609, an n point-spread function is applied to predict pixel values of the subsequent n projection frame based on pixel information from the first frame and the relation between the first frame and the subsequent n projection frame. At step 610, an error residual based on the applied n point-spread function is determined. In some embodiments, the n point-spread function applied is stored in a library of point-spread functions. In those embodiments, different point-spread functions are applied to the first frame and the subsequent n projection frame. At step 611, a different point-spread function is applied if necessary. If more than one point-spread function is applied, at step 612, the point-spread function resulting in the smallest error residual is used to compress the subsequent n projection frame. At step 613, the error residual for the subsequent n projection frame is entropy encoded and an index for the applied point-spread function with the smallest error residual is stored in the subsequent n projection frame, the P-frame. Then at step 614, the process, steps 608-613, is repeated for any subsequent n frames. Once a point-spread function has been applied to all the subsequent n projection frames and the error residuals have been encoded, at step 615, a compressed image data set 620 is created including at least one I-frame and one or more P-frames.

In some embodiments, the compressed data set 620 is a single compressed data file. The compressed data set 620 can also be a plurality of series of compressed image projection frames in separate compressed files. Furthermore, in some embodiments, the compressed data set 620 can be implemented as a data-stream for transmission of a compressed series of related x-ray projection frames.

Figure 4:
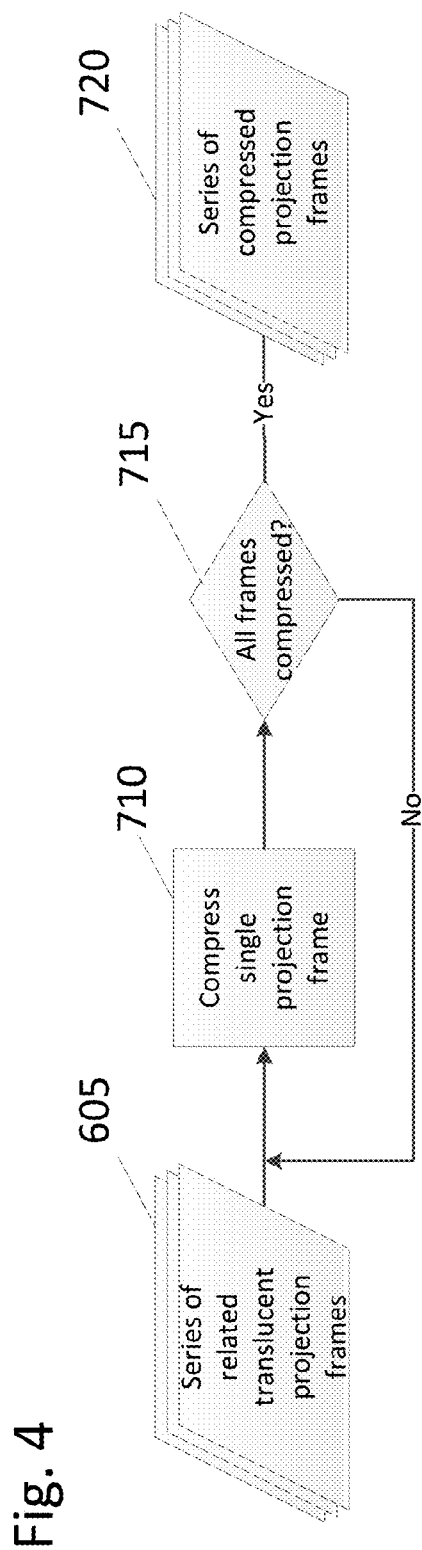
FIG. 4 is a schematic diagram of a compression method that compresses each projection frame individually.

The use of the modified video compression techniques to compress a series of related x-ray image projection frames 605 results in a smaller amount of data to be transferred than individual compression of each raw projection frame in the series. For example, FIG. 4 illustrates a compression method that does not utilize predictive video compression techniques. Thus, each raw projection frame in a series of related x-ray projection frames 605 is compressed individually (step 710) without using a prediction algorithm until all raw projection frames of the series are compressed (step 715). The resulting data is a series of compressed projection-frame data 720 rather than the compressed image data set 620. Accordingly, the use of video compression techniques on a series of related x-ray projection frames 605 results in a greater compression ratio, particularly when the video compression technique utilizes the modified prediction algorithm customized for a series of x-ray projection frames as explained above.

Moreover, the techniques of image compression for individual frames and predictive video compression for the sequence of frames can be combined. For example, the predictive algorithm can be applied to the compressed projection frame data 720, resulting in an even greater compression ratio than if only individual frame compression or only predictive video compression were used.

After the series of related x-ray projection frames 605 is compressed, the hybrid system 100 transfers the compressed image data set 620 between the dental imaging machine 200, the computer 122, the local image devices 125*a-d*, the local server 130, the network 110, and the external image devices 145*a-b*. The local server 130 acts as a cache server that communicates with network 110. As shown in FIG. 1, network 110 allows the local server 130 to communicate with the cloud server 155. In some embodiments, the hybrid system 100 includes more than one cloud server 155. In the illustrated embodiment, the cloud server 155 is a remote server separate from the dental office 115. The external image devices 145*a-b*, in turn, communicate with the cloud server 155. Thus, the hybrid system 100 allows the x-ray image data acquired by the networked imaging system 120 to be accessible to the local image devices 125*a-d*, the local server 130, the cloud server 155, and the external image devices 145*a-b*.

Multiple local image devices 125*b*, 125*c*, and 125*d* are able to communicate to the local server 130 via the LAN 105. This communication allows for data associated with dental images to be transferred between local image devices 125*a-d* of the hybrid system 100 and easily viewed from many local image devices 125*a-d*. Local image devices 125*b*, 125*c*, and 125*d* can be located in separate areas within the dental office 115 from the networked imaging system 120. For example, local image device 125*b* can be located at a front desk of the dental office 115, in an operating room of dental office 115, and/or in a personal office of dental office 115.

A series of related x-ray projection frames 605 to be uploaded from the dental office 115 to the cloud server 155 is first uploaded to the local server 130 via the LAN 105. In the illustrated embodiment, the local server 130 compresses the series of related x-ray projection frames 605 into the compressed image data set 620 as described above (see FIG. 3). In other embodiments, other components of the hybrid system 100 compress the series of x-ray projection frames 605 into the compressed image data set 620. The local server 130 continually synchronizes to the cloud server 155. Upload requests to the cloud server 155 are queued on the local server 130 until upload is achieved. Download requests from the dental office 115 to the cloud server 155 are cached on the local server 130 until the download requests can be fulfilled. Upload and download speeds are increased by the modified video codec 150 that allows for increased compression ratios.

All compressed image data 620 that is uploaded to the cloud server 155 can also be stored on the local server 130 based on a specified policy. For example, the local server 130 can store compressed image data 620 created within the last specified number of months. Alternatively, the local server 130 can also have a policy to store compressed image data 620 created for a specified number of patients. The policy to store compressed image data 620 on the local server 130 can also be based on patient appointment scheduling information. The patient appointment scheduling information can be stored, for example, in an electronic patient scheduling calendar. The patient appointment scheduling information can include information about an amount of time elapsed since the most recent visit of each patient, an amount of time until a next expected visit of each patient, and the like. Thus, the local server 130 can have a policy to store compressed image data 620 from the most recent visit of each patient or a policy to store compressed image data 620 based on a next scheduled appointment of each patient. For example, the local server 130 can store compressed image data 620 if the most recent visit from a patient is within a specified time period, and/or the local server 130 can retrieve compressed image data 620 associated with certain patients from the cloud server 155 when those patients have an appointment the next day. The policy to store compressed image data 620 on the local server 130 can also be based on the most recent access of compressed image data 620 associated with a particular patient. For example, if compressed image data 620 for a particular patient was accessed within a specified period of time, the local server 130 stores the compressed image data 620. The policy to store compressed image data 620 can also be based on an amount of available storage space on the local server 130. For example, if the local server 130 no longer includes available storage space, the local server 130 may delete the oldest image data on the local server 130. In some embodiments, the amount of available storage space overrides other conditions of the policy, for example, the amount of time since the most recent visit, the amount of time until the next scheduled visit, and the like. In other embodiments, the amount of available storage space is only a secondary condition.

When compressed image data 620 stored on the local server 130 no longer falls within the specified policy, the compressed image data 620 is deleted to create availability on the local server 130 for new compressed image data 620 that meets the specified policy. The policy may be based on a number of conditions. Each condition may be assessed individually or in conjunction with another condition. Copies of deleted compressed image data 620 remain stored on the cloud server 155 for later retrieval. A policy may also be in place for determining when to retrieve compressed image data 620 from the cloud server 155. The policy for retrieving compressed image data 620 from the cloud server 155 may also be based on a number of conditions including, for example, a time period of a next expected visit of a patient and a specific user request for specific image data. For example, if a next expected visit of a patient is within a specified period of time, the local server 130 retrieves the compressed image data 620 associated with that patient from the cloud server 155.

The speed of communication using the LAN 105 is generally significantly faster than the speed of communication using the network 110. However, in some cases, the LAN 105 may be difficult or expensive to scale up, and/or may not make the data as widely available as the cloud portion of the system 100. The specified policy allows the hybrid system 100 to be configured by a user to ensure that desired compressed image data 620 is easily and quickly accessible from the local server 130. The hybrid system 100 also provides scalability and wide availability of data through use of the cloud server 155. The cloud server 155 provides reliable back-up of compressed image data 620 and allows access to compressed image data 620 from outside of the dental office 115. As is discussed below in more detail, in some embodiments of the invention, each series of related x-ray projection frames 605 is not compressed and, instead, uncompressed image data 605 is transferred among components of the hybrid system 100.

The hybrid system 100 also supports automatic failover between the local server 130 and the cloud server 155. For example, if the connection to the local server 130 malfunctions, local image devices 125*a-d* and computer 122 can communicate directly with the network 110. For example, a local image device 125*a-d* may determine whether the local server 130 is malfunctioning based on, for example, an amount of time required for the local server 130 to communicate with the local image device 125*a-d*. When the local image device 125*a-d* determines that the local server 130 is malfunctioning, the local image device 125*a-d* then transmits any x-ray image data 605, 620, 720 directly to the cloud server 155. The computer 122 and the local image devices 125*a-d* can also store the x-ray image data 605, 620, 720 until the connection to the local server 130 is restored. Similarly, the cloud server 155 may determine that the local server 130 is malfunctioning and transmit image data 605, 620, 720 directly to a local image device 125*a-d*. The local server 130 can also determine when the connection to the cloud server 155 is malfunctioning. When the connection to the cloud server 155 is malfunctioning, the local server 130 waits to upload/download any x-ray image data 605, 620, 720 until the connection to the cloud server 155 is restored.

Additionally, both the local server 130 and the cloud server 155 support the same application interface. Thus, client software 140 can connect to the local server 130 when inside the dental office 115 or can connect to the cloud server 155 when outside the dental office 115.

External image devices 145*a* and 145*b* can access compressed image data 620 on the cloud server 155 via the network 110 from outside the dental office 115. In the illustrated embodiment, the external image devices 145*a* and 145*b* include a second codec 152 to decompress the compressed image data 620 received from the cloud server 155. In other embodiments, the cloud server 155 may include the second codec 152. The second codec 152 works essentially the same as the codec 150 described above. Additionally, client software 140 on the external image devices 145*a* and 145*b* can compute a three-dimensional volumetric data set based on the compressed image data set 620, 720.

In the embodiment shown, external image device 145*a* is a laptop computer, and external image device 145*b* is a tablet. However, external image devices 145*a* and 145*b* are not limited to a computer or tablet. Other devices capable of communicating with the network 110 can be used. Users of external image devices 145*a* and 145*b* can be notified when a new compressed image data set 620 of interest has been uploaded to the cloud server 155.

FIG. 5 illustrates a block diagram of the steps taken by the hybrid system 100 to upload compressed image data 620 created from a series of related x-ray projection frames 605 from the networked imaging system 120 to the cloud server 155 in one exemplary embodiment. First, the dental imaging machine 200 acquires a series of related x-ray image projection frames 605 (step 305). If the dental imaging machine 200 is connected to the computer 122, the x-ray projection frames 605 are stored on the computer 122 (step 307). Client software 140 on computer 122 then transmits the series of related x-ray projection frames 605 to the local server 130 via the LAN 105 (step 310). The series of related x-ray projection frames 605 is stored on the local server 130 (step 312). Users inside the dental office 115 are then notified that the series of related x-ray projection frames 605 is available (step 315). At this point, any of the local image devices 125*a-d* can connect to the local server 130 and obtain the x-ray projection frames 605. The series of related x-ray projection frames 605 is then compressed into a compressed image data set 620 using a prediction algorithm customized for a series of x-ray projection frames 605 (step 317). The compressed image data set 620 is placed in a queue to be uploaded and stored in the cloud server 155 (step 320). The compressed image data set 620 remains in the queue until the upload is completed (step 325). After the upload is completed, relevant users outside the office are notified that the compressed image data set 620 is available (step 330). At this point, any of the external image devices 145*a-b* can connect to the cloud server 155 and obtain the x-ray image data 620. The hybrid system 100 then retrieves the patient appointment scheduling information for the patients associated with the hybrid system 100 (step 335). The hybrid system 100 then verifies that the x-ray image data 605, 620, 720 stored on the local server 130 still complies with the specified policy (step 340). If the x-ray image data 605, 620, 720 stored on the local server 130 no longer complies with the specified policy, the x-ray image data 605, 620, 720 is deleted from the local server 130 (step 345).

Figure 6:
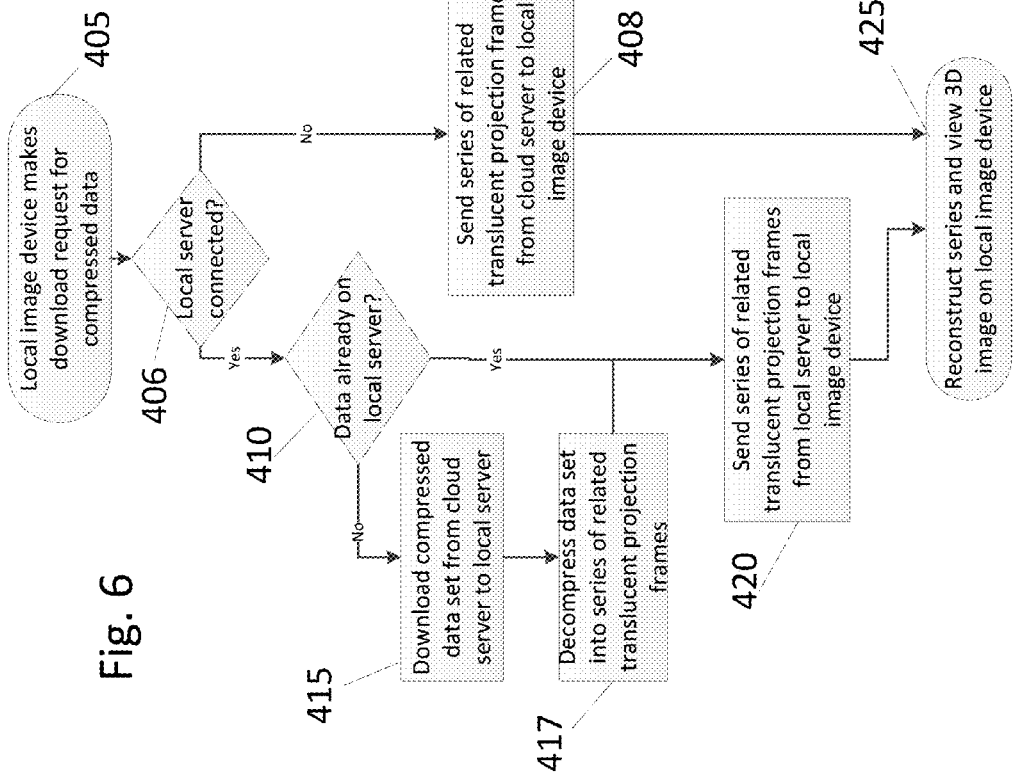
FIG. 6 is a schematic diagram of a method of downloading image data to a local image device from the cloud server implemented by the hybrid system of FIG. 1.

FIG. 6 illustrates a block diagram of exemplary steps taken by the hybrid system 100 to download compressed image data 620 to a local image device 125*a-d*. First, the local image device 125*a-d* makes a download request for a compressed image data set 620 (step 405). The hybrid system 100 then verifies whether the connection to the local server 130 is enables (e.g., the hybrid system 100 is connected), disabled (e.g., the hybrid system 100 is disconnected), or malfunctioning (step 406). If the connection to the local server 130 is disconnected or malfunctioning, the x-ray image data 605, 620, 720 is downloaded directly from the cloud server 155 to the local image device 125*a-d* (step 408). If the connection to the local server 130 is working properly, the hybrid system 100 checks if the requested compressed image data set 620 is already stored on local server 130 (step 410). If the requested compressed image data set 620 is not already located on the local server 130, the compressed image data set 620 is downloaded from the cloud server 155 to the local server 130 (step 415). Next, the downloaded compressed image data set 620 is decompressed (or restored) into a decompressed data set including a series of related x-ray projection frames 605 according to the modified prediction algorithm customized for a series of x-ray projection frames 605 (step 417). Once the decompressed series of raw image projection frames 605 is on the local server 130, the decompressed (or restored) data set 605 is sent from the local server 130 to the local image device 125*a-d* that made the download request (step 420). In the illustrated embodiment, the local image device 125*a-d* then reconstructs the series of related x-ray projection frames 605, computes a three-dimensional volumetric data set based on the series of related x-ray projection frames 605, and displays a three-dimensional volumetric image (step 425). In additional embodiments, the series of raw projection frames can be viewed without computing a three-dimensional volumetric data set.

Figure 7:
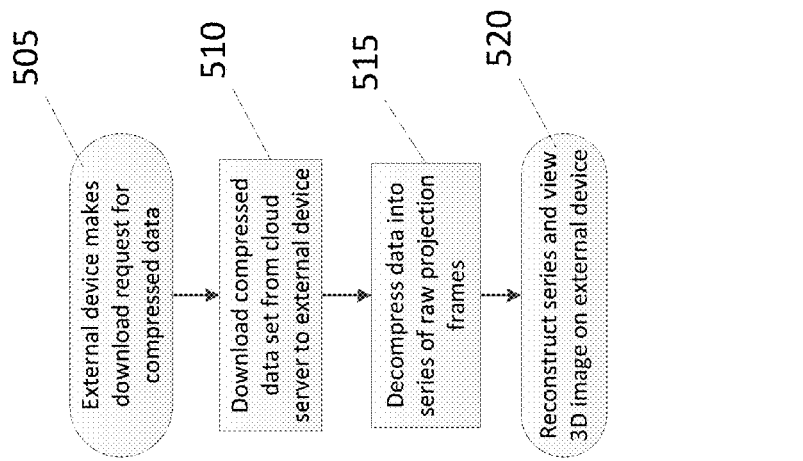
FIG. 7 is a schematic diagram of a method of downloading image data to an external device from the cloud server implemented by the hybrid system of FIG. 1.

FIG. 7 illustrates a block diagram of exemplary steps taken by the hybrid system 100 to download compressed image data 620 to an external image device 145*a-b*. First, the external image device 145*a-b* makes a download request for a compressed image data set 620 (step 505). The compressed image data set 620 is downloaded from the cloud server 155 to the external image device 145*a-b* (step 510). The downloaded compressed image data set 620 is decompressed into a series of related x-ray projection frames 605 according to the modified prediction algorithm customized for a series of x-ray projection frames 605 (step 515). Optionally, if each frame was also previously compressed on a frame-by-frame basis, step 515 can further include frame-by-frame image decompression. In the illustrated embodiment, the external image device 145*a-b* then reconstructs the decompressed series of related x-ray frames 605 and computes a three-dimensional volumetric image data set (step 520). In additional embodiments, the series of related x-ray frames 605 can be viewed without computing a three-dimensional volumetric image data set.

In some embodiments, local image devices 125*a-d* and/or external image devices 145*a-b* may request a plurality of series of related x-ray projection frames 605 and/or compressed data sets 620 associated with multiple series of related x-ray projection frames 605. The plurality of x-ray projection frames 605 and compressed data sets 620 requested by the image devices 125*a-d*, 145*a-b* may be associated with a particular patient (i.e., history of x-rays for a patient) and may be downloaded concurrently.

In the embodiments described so far, the local server 130 communicates directly with the network 110. In additional embodiments, numerous local servers 130 communicate with a cache server (not pictured), which, in turn, communicates with the network 110. Numerous local servers 130 can be located at numerous dental offices 115. For example, a second local server (not pictured) can retrieve and store a series of related x-ray projection frames 605 and/or compressed data sets 620 from the cloud server 155 after the local server 130 uploads the series of related x-ray projection frames 605 and/or compressed image data sets 620. Compressed image data sets 620 and series of related x-ray projection frames 605 can be shared and viewed between dental offices 115.

In one embodiment, the hybrid system 100 can be located in a large facility, for example, a hospital. The large facility can include at least one local server 130 that communicates directly to the network 110. Alternatively, each local server 130 can communicate with a cache server, which, in turn, communicates with the network 110.

In embodiments described so far, compression occurs before placing the image data to be transferred in the upload queue (see step 317). But optionally, compression of the series of related x-ray projection frames 605 (step 317) can occur at any point prior to uploading the compressed image data set 620, 720 to the cloud server 155. Thus, compression can occur after the series of related x-ray projection frames 605 is placed in the upload queue. Alternatively, compression can occur immediately after the series of related x-ray projection frames 605 is acquired and before the series of related x-ray projection frames 605 is transmitted to the local server 130.

In some embodiments, each series of related x-ray projection frames 605 may not be compressed before transmitting image data to the cloud server 155. For example, if a series of related x-ray projection frames 605 is small in data size, the local server 130 may transmit an uncompressed series of related x-ray projection frames 605 to the cloud server 155 to be stored. Accordingly, local image devices 125*a-d* and external image devices 145*a-b* may not perform decompression (steps 417 and 515 respectively) when downloading the uncompressed series of related x-ray projection frames 605 from the cloud server 155.

In embodiments described so far, storage of the series of related x-ray projection frames 605 occurs before compressing the series of related x-ray projection frames 605 (see step 312). But optionally, the local server 130 can compress the series of related x-ray projection frames 605 into a compressed image data set 620, 720 and store the compressed data set 620, 720 on the local server 130.

In some embodiments, local image devices 125*a-d* include a codec in place of or in addition to the codec 150 of the local server 130. Thus, all compression and decompression can occur on local image devices 125*a-d*. Accordingly, only compressed image data sets 620 are transferred within the hybrid system 100.

Thus, embodiments of the invention provide, among other things, systems and methods for storing and accessing medical image data using a local server in combination with a cloud server. The systems and methods make use of improved video compression techniques for use on a series of x-ray, two-dimensional, raw projection frames. The systems and methods allow for quick access to specified data on a local server while also providing scalability and wide availability of data through use of a cloud server.

Various features of the invention are set forth in the following claims.

What is claimed is:

1. A method of processing x-ray data, the method comprising:
    acquiring a plurality of x-ray projection frames of at least one object representing at least a portion of a patient, the plurality of x-ray projection frames including first and second frames; and
    compressing the plurality of x-ray projection frames to generate a compressed data set, wherein the compressing includes predicting at least one pixel of the second frame based on at least one pixel of the first frame;
    providing an x-ray source and an x-ray image detector; the detector configured to output the first and second frames;
    acquiring the first frame while the source and detector are at a first angle with respect to the patient; and
    acquiring the second frame while the source and detector are at a second angle with respect to the patient;
    wherein the first frame includes a first x-ray projection of at least one object within the patient;

wherein the second frame includes a second x-ray projection of the at least one object and wherein compressing the plurality of x-ray projection frames includes using at least the first and second angles to predict values of pixels representing the second x-ray projection in the second frame.

2. The method of claim 1 further comprising computing a three-dimensional volumetric data set from the compressed data set.

3. The method of claim 2, wherein computing a three-dimensional volumetric data set includes decompressing the compressed data set to generate a decompressed data set and computing the three-dimensional volumetric data set based on the decompressed data set.

4. The method of claim 1 wherein compressing the plurality of x-ray projection frames includes processing the first frame with a point spread function to predict the at least one pixel of the second frame.

5. A system for processing x-ray image data, the system comprising:
- an imaging system configured to acquire x-ray image data, the x-ray image data including a plurality of x-ray frames, the plurality of x-ray frames including first and second frames; and
- a codec configured to receive the x-ray image data from the imaging system and compress the plurality of x-ray projection frames to generate a compressed data set, wherein the compressing includes predicting at least one pixel of the second frame based on at least one pixel of the first frame;
- providing an x-ray source and an x-ray image detector; the detector configured to output the first and second frames;
- acquiring the first frame while the source and detector are at a first angle with respect to the patient; and
- acquiring the second frame while the source and detector are at a second angle with respect to the patient;
- wherein the first frame includes a first x-ray projection of at least one object within the patient;
- wherein the second frame includes a second x-ray projection of the at least one object and wherein compressing the plurality of x-ray projection frames includes using at least the first and second angles to predict values of pixels representing the second x-ray projection in the second frame.

6. The system as claimed in claim 5, the system further comprising a computer configured to generate a three-dimensional volumetric data set from the compressed data set.

7. The system of claim 6, wherein the computer is configured to decompress the compressed data set to generate a decompressed data set and compute a three-dimensional volumetric data set based on the decompressed data set.

8. The system of claim 6, wherein the imaging system includes:
- an x-ray source; and
- an x-ray image detector, the detector configured to output the first and second frames,
- wherein the imaging system is configured to acquire the first frame while the source and the detector are at a first angle with respect to the patient, and to acquire the second frame while the source and detector are at a second angle with respect to the patient;
- wherein the first frame includes a first x-ray projection of at least one object within the patient;
- wherein the second frame includes a second x-ray projection of the at least one object; and
- wherein the codec is configured to compress the plurality of x-ray projection frames by using at least the first and second angles to predict locations of pixels representing the second projection in the second frame.

9. The system of claim 5, wherein the codec is configured to compress the plurality of x-ray projection frames by processing the first frame with a point spread function to predict the at least one pixel of the second frame.

* * * * *